United States Patent [19]

Schmidt et al.

[11] Patent Number: 5,010,059
[45] Date of Patent: Apr. 23, 1991

[54] PHARMACEUTICAL PRODUCTS AND LACTOSYL COMPOUNDS

[75] Inventors: Richard R. Schmidt; Thomas Baer, both of Konstanz; Peter Zimmerman, Villingen; Albrecht Wendel, Tübingen, all of Fed. Rep. of Germany

[73] Assignee: Solco Basel AG, Basel, Switzerland

[21] Appl. No.: 210,838

[22] Filed: Jun. 24, 1988

[30] Foreign Application Priority Data

Jun. 26, 1987 [CH] Switzerland ............. 2407/87

[51] Int. Cl.$^5$ .................. A61K 31/70; C07H 15/00
[52] U.S. Cl. ........................ 514/25; 514/53; 536/17.9
[58] Field of Search ............ 514/25, 536, 53; 536/4.1, 17.9, 18.6

[56] References Cited

U.S. PATENT DOCUMENTS 4,442,284  4/1984  Kolar et al. ............. 336/4.1

OTHER PUBLICATIONS

Schmidt et al., Chemical Abstracts, vol. 96 (1982) No. 123141m.
Schmidt et al., Chemical Abstracts, vol. 102 (1985) No. 79236n.
Saito et al., Chemical Abstracts, vol. 107 (1987) No. 94081e.
Schmidt et al., Angew, Chem.-Int. Ed. Engl. 24 (1985) 65-66.

*Primary Examiner*—Johnnie R. Brown
*Assistant Examiner*—Elli Peselev
*Attorney, Agent, or Firm*—Wenderoth, Lind & Ponack

[57] ABSTRACT

The compounds of the formula I exert a pronounced specific cytoprotective effect; they can be used for the treatment of acute and chronic inflammations and organ ischemias caused by narrowing of vessels. $R^1$ denotes an aliphatic radical having 9 to 19 C atoms in the straight chain, $R^2$ denotes the acyl radical of a saturated or unsaturated fatty acid having 14 to 24 C atoms, and X denotes a $-CH_2CH_2-$ or $-CH=CH-$ group. The invention relates to pharmaceutical products in which the active ingredient is the said compounds, as well as to those compounds I in which $R^2$ denotes the acyl radical of an unsaturated fatty acid, and to the process for the preparation thereof.

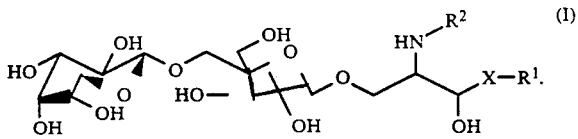

10 Claims, No Drawings

PHARMACEUTICAL PRODUCTS AND LACTOSYL COMPOUNDS

Cerebrosides is the name given to a group of glycolipids which are constructed of ceramides and galactose or glucose and which occur in the cerebral matter and the nerve cells [Sandhoff, Angew. Chem. 89 (1977), 283-295].

There has been particularly thorough investigation of glucosylceramides of the formula:

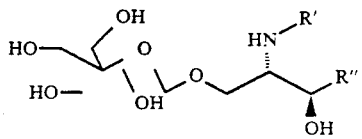

in which R' denotes the acyl radical of a fatty acid having 14 to 24 carbon atoms, and R" denotes the pentadecanyl or heptadecanyl radical $C_{15}H_{31}$ or $C_{17}H_{35}$ or corresponding unsaturated radicals (European Patent Application No. 84 11 4415.7, Publication No. 146 810). They are prepared by a total synthesis starting from racemic or optically active ceramides.

When a racemic starting material is used, it is necessary at a particular stage in the process to separate the resulting diastereomers. The optically active ceramides in turn are obtained from the corresponding sphingosines, which are accessible only by a tedious route which is unsatisfactory in terms of yield.

The same glucosylceramides can also be prepared, with better yield and without separation of diastereomers, from commercially available D-galactose or from D- or L-xylose by another synthesis process (European Patent Application No. 86 11 0694.6, Publication No. 212 400).

It has been possible in the same way to synthesize a lactosylceramide having a palmitoyl radical as acyl radical; nothing further is known about this compound, especially about any pharmacological properties [R.R. Schmidt et al., Angew. Chem. 98 (1986), 722-723].

In fact, the abovementioned lactosylceramide, and others having a saturated acyl radical on the nitrogen atom in each case, have been prepared previously [D. Shapiro et al., Nature 201 (1964), 878-879; Chem. Phys. Lipids -1 (1966), 54-62], but have not undergone detailed pharmacological investigation; this was because the synthesis was meant to confirm a structural formula assigned to a natural product.

The galactosylceramides and the glucosylceramides are all, without exception, distinguished by effects promoting wound healing and cell and tissue regeneration, and they can be used therapeutically for the treatment of wounds of any origin.

It has now been found that lactosyl compounds of the formula I (on the annexed formula sheet) unexpectedly differ markedly in their pharmacological behavior from the pattern of effects described above, in that they do not act primarily on damaged cells and tissues to promote healing and regeneration but, rather, exert a specific cytoprotective effect against damaging inflammatory actions.

Thus the invention relates to pharmaceutical products which contain as active ingredient at least one lactosyl compound of the general formula I and are intended for use as cytoprotective agents, especially for the prophylaxis of cell and tissue damages of non-traumatic origin. In the formula I, $R^1$ denotes an aliphatic radical which has 9 to 19 carbon atoms in the straight chain and can have one or more double bonds and/or branching methyl groups, $R^2$ denotes the acyl radical of a saturated or singly or multiply unsaturated fatty acid having 14 to 24 carbon atoms, and X denotes a group of the formula $-CH_2-CH_2-$ or $-CH=CH-$.

The invention further relates to the new lactosyl compounds of the general formula IA in which $R^1$ and X have the same meaning as in formula I, and $R^{2'}$ represents the acyl radical of a singly or multiply unsaturated fatty acid having 14 to 24 carbon atoms.

The lactosyl compounds are derivatives of sphingosine and, depending on the stereochemical configuration of the basic sphingosine molecule, belong to the erythro or the threo series. In terms of their stereochemistry, the erythro compounds correspond to the naturally occurring neutral glycosphingolipids which are already known. To illustrate the stereochemical relationships, reference may be made to the four possible configurations of sphingosine:

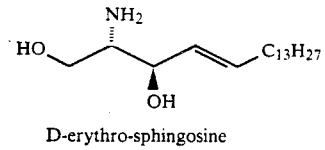

D-erythro-sphingosine

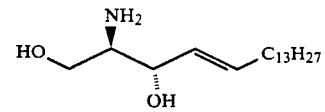

L-erythro-sphingoshine

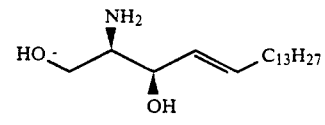

D-threo-sphingosine

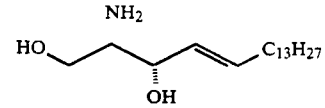

L-threo-sphingosine

Among the aliphatic chains $R^1$, those with 13 to 15 carbon atoms are preferred. These chains have, where appropriate, one or more double bonds, for example one such in the 3,4 position, or double bonds in the 3,4 and 7,8 positions. It is also possible for the aliphatic chain to have one or more, say up to 4, branching methyl groups, for example in the 4 position or on the terminal carbon atom.

Examples of the saturated acyl radicals $R^2$ are the acyl radicals of myristic acid $C_{14}H_{28}O_2$, of palmitic acid $C_{16}H_{32}O_2$, of stearic acid $C_{18}H_{36}O_2$ and of arachidic acid $C_{20}H_{40}O_2$. Examples of the unsaturated acyl radicals $R^2$ and $R^{2'}$ which may be mentioned are the acyl radicals of palmitoleic acid $C_{16}H_{30}O_2$ (cis-9-hexadecenoic acid), of oleic acid and of elaidic acid $C_{18}H_{34}O_2$ (cis-9- and trans-9-octadecenoic acid, respectively), of linoleic acid $C_{18}H_{32}O_2$ (cis,cis-9,12-octadecadienoic acid), of linolenic acid and of eleostearic acid $C_{18}H_{30}O_2$ (9,12,15- and 9,11,13-octadecatrienoic acid, respectively), of arachidonic acid $C_{20}H_{32}O_2$ (5,8,11,14-eicosatetraenoic acid), of eicosapentaenoic acid $C_{20}H_{30}O_2$, of erucic acid and of brassidic acid $C_{22}H_{42}O_2$ (cis-13- and trans-13-docosenoic acid, respectively) and of nervonic acid $C_{24}$-$H_{46}O_2$ (cis-15-tetracosenoic acid). Preferred acyl radicals are those with an even number of carbon atoms in the chain, especially the $C_{16}$, $C_{18}$ and $C_{20}$ radicals.

The products which are very generally preferred are those in which the acyl radical $R^2$ in the active ingredient of the formula I therein is that of palmitic acid, of oleic acid, of linoleic acid, of linolenic acid., of arachidonic acid and of eicosapentaenoic acid, and the aliphatic radical $R^1$ therein has 13 to 15 carbon atoms in the straight chain.

Various pharmacological tests can be used to test for any therapeutically beneficial effect on damaged cells and tissues. An action promoting healing can be estimated and measured, in particular, by using the so-called skin flap test; the test is based on the development of a cutaneous necrosis and the inhibition thereof as a consequence of the action of the test substance.

Male Wistar rats of body weight 220–240 g in groups of 8 animals for each value which is to be determined are anesthetized with Nembutal (50 mg/kg, i.p.). A 1×3 cm skin flap is cut out, using a scalpel, from the back, is thoroughly washed and is returned to the original site and is sutured. The test animals are given the compound which is to be tested, in 5% concentration in aqueous solution (containing 0.2% ethanol and 1% polyethylene glycol of molecular weight 20,000—or Carbowax ®20; in each case 1.5 ml intraperitoneal), each day for 8 days; the control animals receive only the aqueous medium. Each day drawings are made of the skin flaps on the scale 1:1, with the necrotic sites being colored black. The animals are sacrificed after 8 days, and the drawings are evaluated using a Biotran apparatus, and the total area of the necrotic sites is measured in mm² The action promoting healing is expressed as the increase in the area of surviving skin as a percentage compared with the control.

The abbreviations in the present description have the following meanings:

| | |
|---|---|
| Glu: D-glucosyl | Pal: acyl radical of palmitic acid |
| Gal: D-galactosyl | OL: acyl radical of oleic acid |
| Lac: D-lactosyl | Linol: acyl radical of linoleic acid |
| | Linolen: acyl radical of linolenic acid |

-continued

| | |
|---|---|
| | Arach: acyl radical of arachidonic acid |
| Sph: basic structure of $C_{18}$-sphingosine | |

TABLE 1

| | Action promoting heating in the skin flap test | | | | | |
|---|---|---|---|---|---|---|
| | Area of the skin flap | Area of the necrotic skin | | Area of surviving skin | | Action of the compound |
| Compond | in mm² | in mm² | in % | in mm² | in % | in % |
| Glu(Pal)-D-Sph | 257.4 ± 6.2 | 113.3 ± 10.6 | 43.8 | 144.1 ± 9.1 | 56.2 | +30.1% |
| Glu(Pal)-L-Sph | 264.4 ± 2.6 | 85.8 ± 14.7 | 32.7 | 178.6 ± 16.8 | 67.3 | +55.8% |
| Control | 259.5 ± 4.9 | 146.6 ± 17.3 | 56.8 | 112.9 ± 19.1 | 43.2 | — |
| Glu(Linolen)-D-Sph | 291.5 ± 5.5 | 184.1 ± 28.9 | 62.8 | 107.4 ± 27.3 | 37.2 | +144.7% |
| Control | 301.0 ± 4.1 | 155.5 ± 14.5 | 84.8 | 45.5 ± 12.7 | 15.2 | — |
| Gal(Pal)-D-Sph | 273.3 ± 5.2 | 81.4 ± 18.5 | 29.8 | 191.8 ± 18.9 | 70.2 | +31.2% |
| Gal(Pal)-L-Sph | 281.3 ± 7.6 | 84.5 ± 13.6 | 30.1 | 196.8 ± 15.2 | 69.9 | +30.7% |
| Control | 267.9 ± 5.4 | 125.0 ± 27.3 | 46.5 | 142.9 ± 26.6 | 53.5 | — |
| Lac(Pal)-D-Sph | 310.9 ± 6.9 | 113.2 ± 13.0 | 36.2 | 197.6 ± 12.6 | 63.8 | +47.3% |
| Lac(Pal)-L-Sph | 295.5 ± 6.4 | 112.7 ± 13.3 | 37.7 | 182.8 ± 11.3 | 62.3 | +43.9% |
| Control | 301.3 ± 10.9 | 172.6 ± 27.4 | 56.7 | 128.7 ± 22.5 | 43.3 | — |
| Lac(Linolen)-D-Sph | 324.0 ± 10.0 | 128.1 ± 34.2 | 39.6 | 195.9 ± 35.5 | 60.4 | +22.0% |
| Control | 324.6 ± 8.8 | 164.3 ± 22.2 | 50.5 | 160.3 ± 20.6 | 49.5 | — |
| Lac(Arach)-D-Sph | 323.1 ± 10.4 | 111.5 ± 25.8 | 35.8 | 211.6 ± 33.3 | 64.1 | +36.8% |
| Control | 302.6 ± 8.6 | 158.5 ± 19.3 | 52.8 | 144.1 ± 20.9 | 47.1 | — |

The results reproduced above show that the compounds investigated have a distinct, and most have in fact a pronounced, action promoting healing, and this applies both to the group of lactosylceramides and to the group of glucosyl- and galactosylceramides used for comparison.

In order to gain a deeper insight into the pharmacological properties of the compounds of the formula I, they have been examined for any cytoprotective effects they may have. The cytoprotective effect can be shown, inter alia, by the method described by A. Wendel and G. Tiegs in Biochemical Pharmacology 35 (1986), 2115–2118. This is based on the impairment of liver function as a consequence of sensitization of the liver due to administration of D-galactosamine and simultaneous treatment with endotoxins.

D-galactosamine (abbreviated to GalN) causes in animals liver damage which is regarded as a model for human viral hepatitis. The mechanism is assumed to be an accumulation of toxic galactosamine derivatives in the liver, which results in a diminution in the biosynthesis of macromolecules such as ribonucleic acids, proteins, glycoproteins and glycogens. These changes in the metabolism may in turn result in cell damage or even death of cells in the liver. The extent of liver damage can be determined by the increase in certain liver enzymes (sorbitol dehydrogenase SDH, serum glutamic-oxalic transaminase SGOT, serum glutamic-pyruvic transaminase SGPT) in the blood and by histology of the liver.

When lipopolysaccharides (LPS, endotoxins from Gram-negative bacteria) are administered simultaneously with D-galactosamine in a dose which is insufficient to elevate the transaminases (subtoxic dose), the lethal effect of the LPS may be increased by a factor of up to 100,000. The mechanisms of the galactosamine-induced sensitization for the effect of LPS are unknown. However, the most recent investigations suggest that the endotoxins release a number of endogenous mediators (leukotrienes, tumor necrosis factor, prostaglandins, lysosomal enzymes, etc.) from macrophages, and these have a pathogenic effect on previously damaged hepatocytes.

These findings are of clinical interest because they show that an intrinsically innocuous endotoxemia may have a lethal outcome where there is liver damage (for example alcoholic cirrhosis of the liver).

It was also already known that certain substances exert a protective effect against the said liver damage when they are administered to the experimental animal either before or shortly thereafter. This cytoprotective effect has been attained with, inter alia, antiinflammatory agents, leukotriene antagonists, lipoxygenase inhibitors and calcium/calmodulin antagonists, as reported by G. Tiegs and A. Wendel in Biochemical Pharmacology 1988 (in press) and is illustrated in the following Table 2 by the example of known antiinflammatory agents and of diethylcarbamazine.

TABLE 2

Effect of antiinflammatory agents on GalN/endotoxin hepatitis (from A. Wendel, loc. cit.)

| Type of treatment | Number of experimental animals | SGOT | SGPT |
|---|---|---|---|
| No treatment (basal values) | 10 | 90 ± 10 | 70 ± 30 |
| Control (GalN/endotoxin) | 54 | 5,580 ± 5,120 | 10,440 ± 8,640 |
| Indomethacin 9 mg/kg | 8 | 480 ± 475* | 730 ± 1,040* |
| Diethylcarbamazine 78 mg/kg, i.p.[1] | 10 | 270 ± 90** | 290 ± 180** |
| Dexamethasone 200 µg/kg. i.p. | 8 | 140 ± 100* | 100 ± 60** |

Significance:
*p ≤ 0.01
**p ≤ 0.001
[1]every 45 minutes, between 0 and 6 hours

In general, substances likely to be effective in this respect are those which inhibit the formation or release of endogenous mediators from macrophages, activate the reticuloendothelial system or hinder the response of damaged cells to these mediators (cytoprotective effect in the narrower sense).

Surprisingly, this applies to the lactosyl derivatives of the formula I but not to the glycosyl and galactosyl derivatives which were also tested for comparison, as is evident from Table 3 which follows. The test is carried out as follows.

Male albino mice of the NMRI strain are pretreated intraperitoneally with 200 µg/kg test substance and, 1 hour thereafter, treated intraperitoneally with 700 mg/kg D-galactosamine and 33 µg/kg endotoxins. 9 hours later, blood is removed by cardiac puncture, and the enzymatic activity in the blood serum is determined according to H. U. Bergmeyer [Methods in Enzymatic Analysis, 3rd edition (1985), volume III]. In this experimental model, the hepatocytes (Kupffer cells) actually function as immobilized macrophages.

The content of the liver enzymes SDH, SGOT and SGPT in the serum is expressed in international units (IU) for the enzyme activity; 1 IU = 1 µmol of substrate converted/minute in one liter.

TABLE 3

Effect of the compounds I on GalN/endotoxin hepatitis

| Type of treatment | Number of experimental animals | SDH in IU/liter | SGOT in IU/liter | SGPT in IU/liter |
|---|---|---|---|---|
| No treatment (basal values) | 6 | 40 ± 10 | 75 ± 40 | 40 ± 10 |
| Control (GalN/endotoxin) | 14 | 3290 ± 3150 | 1540 ± 1240 | 4230 ± 4120 |
| Glu(Pal)-D-Sph | 8 | 4720 ± 2320[n.s.] | 910 ± 425[n.s.] | 3950 ± 2260[n.s.] |
| Glu(Pal)-L-Sph | 8 | 1690 ± 1680[n.s.] | 410 ± 360[n.s.] | 1470 ± 1460[n.s.] |
| Glu(Linolen)-D-Sph | 8 | 2280 ± 355[n.s.] | 940 ± 170[n.s.] | 3350 ± 630[n.s.] |
| Gal(Pal)-D-Sph | 8 | 2400 ± 2800[n.s.] | 1030 ± 1150[n.s.] | 2990 ± 3510[n.s.] |
| Gal(Pal)-L-Sph | 8 | 4610 ± 6070[n.s.] | 1410 ± 1900[n.s.] | 4730 ± 6210[n.s.] |
| Lac(Pal)-D-Sph | 6 | 80 ± 30* | 80 ± 20** | 110 ± 70* |
| Lac(Pal)-L-Sph | 7 | 80 ± 20* | 120 ± 80** | 80 ± 20* |
| Lac(Linolen)-D-Sph | 7 | 290 ± 250** | 124 ± 55* | 230 ± 76* |
| Lac(Arach)-D-Sph | 6 | 355 ± 425* | 280 ± 260* | 290 ± 210* |

Significance:
[n.s.]not significant
*p ≤ 0.05
**p ≤ 0.01

The protective effect of the lactosyl compounds against the said liver damage is impressively evident from comparison of the normal SDH, SGOT and SGPT values (no treatment) with those after the treatment with galactosamine/endotoxin and with and without pretreatment with the test substance; this effect is significant.

The excellent efficacy of the lactosyl compounds as cytoprotective agents was all the more surprising since the glucosyl and galactosyl compounds proved to be ineffective in this test: from the similar positive effect of all the said compounds in the skin flap test (see Table 1 above), a similar pharmacological behavior is expected to be likely here too.

The specific cytoprotective effect of the lactosyl compounds is evident particularly against damaging inflammatory actions on endothelial cells. This effect is not, however, limited to effective prevention of the onset of inflammatory processes in the body as a consequence of damage; additionally there is suppression of overshoot pathological reactions which lead to a primary inflammation which has already occurred being transformed into a chronic state. Thus, the cytoprotective properties are displayed both curatively, with regard to the primary inflammation, and prophylactically, by preventing the pathological processes from progressing and becoming chronic.

The products according to the invention are thus suitable for use as cytoprotective agents, especially for protection of the endothelial cells from damaging inflammatory actions. These do not, of course, include cuts, contusions, crush injuries and other similar traumatic injuries.

The therapeutic indications are regarded as being, on the one hand, acute and chronic inflammations and, on the other hand, organ ischemias caused by narrowing of vessels, such as apoplectic shock, myocardial infarct and renal infarct. Examples of the said inflammations are hepatitis, polyarthritis, rheumatoid arthritis, myocarditis, inflammatory skin disorders, psoriasis and lupus erythematosus.

Suitable for the prophylactic and curative treatment in the said indications for an adult human is a dose range of about 50 ng/kg to 10 mg/kg of body weight. The single dose administered to a human of 70 kg is preferably an amount of about 1 μg to 50 mg. It is possible and advantageous for administration to be parenteral, in particular intramuscular and intravenous, or topical. Corresponding dosage forms are injectable solutions, ointments and gels.

As is known, the treatment for the indications listed above has to last a long time before the therapy has success; long-term treatment is the rule with prophylactic administration of the products according to the invention. It is thus crucially important that the compounds of the formula I still do not bring about any toxic symptoms or side effects at a dose which is 100 times the effective dose.

This is particularly evident from the acute toxicity testing of the compound Lac(Pal)-L-Sph—exact chemical name: (2R,3S,4E)-1-[4-0-(8-D-galactopyranosyl)-β-D-gluco-pyranosyloxy]-2-hexadecanoylamino-4-octadecen-3-ol. Two groups each of ten mice were observed and weighed each day for 10 days. The animals in the control group each received intraperitoneal administration of 500 μl of a 5 mmol/l solution of Pluronic ® F 68 (manufactured by BASF Wyandotte, Erbslöh/FRG) in physiological saline, while those in the test group received 500 μl of a solution of 6 mg of the compound named above in 6 ml of Pluronic ® F 68. The weight gain in the two groups is illustrated by the following table.

TABLE 4

| Animal No. | Weight on May 10, 1988 | Weight on May 20, 1988 | Difference (in g) | |
| --- | --- | --- | --- | --- |
| 1. | 26.8 | 32.4 | +5.6 | |
| 2. | 27.7 | 34.1 | +6.4 | |
| 3. | 29.4 | 34.2 | +4.8 | |
| 4. | 27.5 | 33.2 | +5.7 | |
| 5. | 30.0 | 35.7 | +5.7 | Control group |
| 6. | 27.0 | 32.1 | +5.1 | |
| 7. | 30.4 | 38.1 | +7.7 | |
| 8. | 29.5 | 33.3 | +3.8 | |
| 9. | 27.3 | 36.6 | +9.3 | |
| 10. | 31.2 | 37.2 | +6.0 | |
| 1. | 29.1 | 35.7 | +6.6 | |
| 2. | 27.0 | 33.0 | +6.0 | |
| 3. | 27.7 | 35.0 | +7.3 | |
| 4. | 27.9 | 34.9 | +7.0 | |
| 5. | 26.7 | 34.4 | +7.7 | Test group |
| 6. | 30.2 | 39.9 | +9.7 | |
| 7. | 24.5 | 28.8 | +4.3 | |
| 8. | 27.6 | 34.0 | +6.4 | |
| 9. | 26.6 | 30.5 | +3.9 | |
| 10. | 26.3 | 31.9 | +5.6 | |

No mortality and no toxic signs were observed during the experiment and the days which followed, nor were any special reactions immediately after the injection; the two animal groups behaved strictly comparable in respect of weight gain. The dose administered to each mouse was about 20 mg/kg, that is to say 100 times the effective dose (200 μg/kg) in the galactosamine/endotoxin test (see above).

The invention also relates to the process for the preparation of the new lactosyl compounds of the formula IA (see formula sheet).

The process comprises reacting an azido compound of the formula II in which R denotes hydrogen or a protective group, and $R^1$ and X have the above meanings, with the O-trifluoro- or O-trichloro-acetimidate or the 1-halogeno or 1-thio derivative of a lactose whose hydroxyl groups in the 2, 3, 6, 2', 3', 4' and 6' positions are protected by acyl groups Ac, eliminating from the resulting compound of the formula III the acyl groups Ac and, where present, the protective group R, converting the azido group in the resulting compound of the formula IV into a primary amino group, and subjecting the resulting compound of the formula V to an N-acylation with a fatty acid $R^{2'}$—OH or a reactive derivative thereof.

The preparation process according to the invention is explained in detail hereinafter.

The starting materials used are azido compounds II whose hydroxyl group in the 3 position is in the free form or in protected form. Particularly suitable protective groups R are simple aliphatic carboxylic acids and aromatic, especially monocyclic aromatic, carboxylic acids; use of benzoic acid, of a substituted benzoic acid or of pivalic acid is preferred. The starting materials II of the erythro series are prepared by the process described in EP 212,400.

The reaction of the compound II with the O-trichloro- or O-trifluoro-acetimidate of a lactose whose hydroxyl groups, apart from that in the 1 position, are protected by acyl radicals Ac is advantageously catalyzed by a Lewis acid such as boron trifluoride etherate or trimethylsilyl trifluoromethanesulfonate. It is generally carried out in an anhydrous organic solvent such as a hydrocarbon (hexane) or a halogenated hydrocarbon (dichloromethane). The acyl radicals preferably used to protect the hydroxyl groups in the 2, 3, 6, 2', 3', 4' and 6' positions of the lactose are lower aliphatic acyl groups such as the acetyl, propionyl, pivaloyl, trifluoroacetyl or methanesulfonyl group. Details of the preparation of the reagent are to be found in the papers by R. R. Schmidt and M. Stumpp (Liebigs Ann. Chem. 1983, 1249–1256) and R. R. Schmidt, J. Michel and M. Roos (Liebigs Ann. Chem. 1984, 1343–1357).

The corresponding reaction with the 1-halogeno derivative of the acylated lactose, for example with the chloride or bromide, is, as a rule, carried out in the presence of a heavy metal compound such as silver oxide, of a heavy metal salt, such as silver carbonate or mercury cyanide, or of an organic base, which act as acid-binding agents (Ullmanns Enzyklopädie der technischen Chemie (Ullmann's Encyclopedia of Industrial Chemistry) 4th edition, volume 24, page 757, Verlag Chemie GmbH, Weinheim FRG 1983). The reaction with the 1-thio derivative is advantageously carried out in the presence of an acid.

The elimination of the acyl radicals Ac and of the protective group R from the compound III is generally catalyzed by bases; particularly expedient for this purpose is the use of sodium methanolate in anhydrous methanol at room temperature.

In the penultimate stage of the process, the best way of converting the azido group into the primary amino group is by treatment of the compound IV with hydrogen sulfide at room temperature. For this purpose, the compound is dissolved, for example, in a mixture (1:1) of water and pyridine. The same conversion can also be carried out by hydrogenation with sodium borohydride or another reducing agent such as, for example, sodium cyanoborohydride.

The N-acylation of the compound V with the organic carboxylic acid of the formula $R^{2'}$—OH (last stage of the process) can be carried out by the method of D. Shapiro and coworkers [J. Am. Chem. Soc. 86, 4472 (1964)]. In general, the carboxylic acid itself will be used in the presence of a water-zemoving agent such as dicyclohexylcarbodiimide in dichloromethane, or a functional reactive derivative of the carboxylic acid will be used, such as an activated ester or a halide in the presence of an inorganic base such as sodium acetate or a tertiary organic base. The N-acylation is advantageously carried out at room temperature.

The compounds resulting at each stage of the process are isolated and purified by the customary methods of organic chemistry.

The examples which follow illustrate preferred embodiments of the invention.

$^1$H NMR spectra were recorded with a WM 250 Cryospec 250 MHz apparatus from Bruker, Spectrospin, Industriestrasse 26, CH-8117 Fällanden/Zurich. The shifts are related to tetramethylsilane (TMS) as internal standard and are reported in ppm.

The reported melting points were determined on a copper block and have not been corrected.

Silica gel plates supplied by E. Merck AG, Darmstadt (FRG) were used for analytical thin-layer chromatography (TLC). For substances not active under UV, the thin-layer chromatograms were sprayed with 15% sulfuric acid and developed at 120° C.

Preparative column chromatographies were carried out with silica gel 60 (0.062–0.200 mm) from E. Mezck AG. Columns prefilled with "LiChroprep Si 60, 15–25" silica gel were used for medium pressure chromatography.

The yields have been reported at the stage of purity where no impurities were detectable by NMR spectroscopy or thin-layer chromatography.

The figures in parentheses for the solvent mixtures denote parts by volume.

Preparation of the Starting Materials 2,3,6,2',3',4',6'-Hepta-O-acetyl-α-D-lactosyl trichloroacetimidate—compound (1)—is prepared as described in Liebigs Ann. Chem. 1984, 1343–1357.

(2S,3R)-2-Azido-3-benzoyloxy-1-hydroxy-4-transoctadecene—compound (2)—is prepared as described in EP 212,400, page 22.

General procedure for the preparation of the carbonyl chlorides of the formula $R^{2'}CL$, namely:
9-cis-octadecenoyl chloride—compound (6)
9-cis-12-cis-octadecadienoyl chloride—compound (7)
9-cis-12-cis-15-cis-octadecatrienoyl chloride—compound (8)

6 mmol of the unsaturated carboxylic acid are refluxed with 2.25 g (18 mmol) of freshly distilled oxalyl chloride at 70° C. with exclusion of moisture. After a reaction time of 4 hours, excess oxalyl chloride is removed by heating the solution up to 70° C. in vacuo.

5-cis-8-cis-11-cis-14-cis-Eicosatetraenoyl chloride—compound (9)

50 mg (164 μmol) of arachidonic acid are refluxed with 40 mg (320 μmol) of freshly distilled oxalyl chloride in 3 ml of anhydrous benzene under a protective atmosphere of N$_2$ gas for 4 hours. The reaction solution is then concentrated, and excess oxalyl chloride is removed at 80° C. in vacuo.

EXAMPLE 1

(2S,3R)-2-(9-cis-Octadecenoylamino)-3-hydroxy-1-(β-D-lactosyloxy)-4-trans-octadecene (10)

(2S,3R)-2-Azido-3-benzoyloxy-1-(2,3,6,2',3',4',6'-hepta-O-acetyl-β-D-lactosyloxy)-4-trans-octadecene (3)

1 g (2.33 mmol) of compound (2) and 2.75 g (3.66 mmol) of lactosyl trichloroacetimidate (1) are dissolved in 50 ml of anhydrous carbon tetrachloride. 4Å molecular sieves which have previously been heated under high vacuum are added to the solution which is then vigorously stirred at room temperature for some minutes. Successive additions, totaling 1.1 ml, of a 0.1 molar solution of boron trifluoride etherate in methylene chloride over a period of 4 hours results in the initially formed ortho ester reacting to give the glycoside (3) (checked by thin-layer chromatography, abbreviated to TLC hereinafter). On cleavage of the ortho ester newly produced compound (2) is captured by addition of a spatula tip of lactosyl trichloroacetimidate (1).

The reaction solution is poured into 150 ml of petroleum ether, the precipitated trichloroacetamide is filtered off, and the filtrate is neutralized with saturated NaHCO$_3$ solution. The organic phase is separated off, dried over magnesium sulfate and concentrated in vacuo. The product is purified by column chromatography (silica gel; petroleum ether/ethyl acetate 65:35).

Yield: 2.1 g (85% based on compound 2) of colorless oil

TLC: (Petroleum ether/ethyl acetate 6:4)

| | | |
|---|---|---|
| | $R_f = 0.46$ | glycoside (3) |
| | $R_f = 0.41$ | ortho ester |
| $[\alpha]_D^{20} = -22.3°$ | (C = 3.8, CHCl$_3$) | |

$^1$H NMR (CDCl$_3$) δ=8.06–7.42 (m,5H,C$_6$H$_5$—), 5.96–5.85 (m,1H,—CH$_2$—CH$_2$—CH=CH—), 5.65–5.48

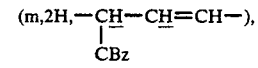

5.35–5.34 (d, 1H,4'-H, J=2.7 Hz), 5.23–5.07 (m,2H,2'-H,3-H), 4.98–4.89 (m,2H, 2H,3'-H), 4.53–4.45 (m,3H,1-H,1'-H,4-H), 4.12–4.02 (m, 3H,CH$_2$O,5'-H), 3.97–3.79 (m,4H), 3.65–3.54 (m,2H), 2.20–1.96 (m,23H,7-CH$_3$,CH=CH—CH$_2$), 1.37–1.24 (m,22H, 11—CH$_2$—), 0.90–0.85 (t,3H,CH$_3$—CH$_2$—)

Analysis for C$_{51}$H$_{73}$O$_{20}$N$_3$ (molecular weight 1048.15): calculated: C 58.44; H 7.02; N 4.01; found: 58.35; 7.08; 3.99.

(2S,3R)-2-Azido-3-hydroxy-1-(β-D-lactosyloxy)-4-transoctadecene (4)

0.5 ml of a 1 molar sodium methanolate solution in methanol is added dropwise to a solution of 5.9 g (5.65 mmol) of compound (3) in 130 ml of anhydrous methanol (TLC check). After the reaction solution has been stirred at room temperature for 4 hours Amberlite ion exchanger (IR 120, H+form) which has been washed several times with methanol to remove acid is added, and the mixture is stirred until neutralization is complete.

Concentration of the solution results in a virtually quantitative yield of a colorless oil.

Yield: 3.6 g (99%)
TLC: (Chloroform/methanol 6:4)   Rf = 0.61
                                  Rf = 0.70 (monoacetyl compound)

(2S,3R)-2-Amino-3-hydroxy-1-(β-D-lactosyloxy)-4-transoctadecene (5)

3.6 g (5.6 mmol) of compound (4) are dissolved in 50 ml of pyridine and 70 ml of water. While stirring, hydrogen sulfide evolved from sodium bisulfide with concentrated hydrochloric acid is passed through for 10 min. The reaction is complete after stirring at room temperature for 18 hours. The solution is concentrated, and the product is purified by chromatography (chloroform/methanol/water 9:1:0 -> 8:2:0 -> 5:4:1).

Yield: 3.28 g (95%) of colorless crystals, slow decomposition above 110° C. observed on determination of the melting point.

TLC: (Chloroform/methanol/water 5:4:1) $R_f$=0.71

$[\alpha]_D^{20} = -8.9°$   (c = 1.2, Pyridine)

$^1$H NMR (DMSO-d6) 5.57 (m,1H,HC=CH—CH$_2$), 5.45 (dd,1H,HC=CH—CH—CH, J=15.5 Hz,J=6.7 Hz), 5.12 (s,1H,OH), 4.82–4.47 (m,6H,6OH), 4.25–4.15 (m,2H), 3.86–2.77 (m,21H, 14 sugar protons,—O—CH$_2$—,CH-NH$_2$,HC=CH—CH—OH),  2.01–1.95 (m,2H,HC=CH—CH$_2$—), 1.33–1.20 (m,22H, 11—CH$_2$—), 0.85 (t,3H,CH$_3$—).

(2S,3R)-2-(9-cis-Octadecenoylamino)-3-hydroxy-1-(β-D-lactosyloxy)-4-trans-octadecene (10)

By the acid chloride method from compounds (5) and (6):

A fine suspension of 310 mg (500 μmol) of compound (5) in 35 ml of tetrahydrofuran is prepared, and 18 ml of a saturated sodium acetate solution are added. While stirring vigorously, 500 μmol of the acid chloride (6) are slowly added dropwise. The reaction is complete after 10–30 min. (TLC check). The reaction mixture is diluted with 200 ml of tetrahydrofuran, the aqueous phase is separated off, and the organic is washed with saturated NaCl solution. The solution is dried over MgSO$_4$ and then evaporated to dryness under water pump vacuum.

The product is purified either (a) via acetylation/deacetylation steps (see Annex, compounds 16 and 17) or (b) by reversed phase medium pressure chromatography (nbutanol/methanol/water 50:32:18). The product is obtained as a colorless foam.

Yield: a) 271 mg (61%) b) 324 mg (73%)
TLC: (Chloroform/methanol 8:2) $R_f$=0.32
Melting point: slow decomposition above 210° C.

$[\alpha]_D^{20} = -10.2°$   (c = 1.0, Pyridine)

Compound (10):
$^1$H NMR (DMSO-d6) 7.54(d,1H,NH,J=8.8 Hz), 5.57–5.49 (m, 1H, HC=CH—CH$_2$), 5.39–5.30 (m,3H,HC=CH—CH—OH, HC=CH), 5.16 (d,1H OH,J=3.7 Hz), 5.12 (d, 1H,OH), 4.90 (d,1H,OH,J=5.5 Hz), 4.84 (d, 1H,OH,J=3.1 Hz), 4.68 (m,2H, OH), 4.63–4.54 (m,2H,OH), 4.22–3.29 (m,17H), 3.09–3.02 (m,1H), 2.06–1.96 (m,8H,COCH$_2$,HC=CH—CH$_2$, CH$_2$—CH=CH—CH$_2$), 1.48–1.23 (m,44H,—CH$_2$—), 0.91–0.83 (t,6H,CH$_3$—).

Analysis for C$_{48}$H$_{89}$O$_{13}$N.1.0 H$_2$O (Molecular weight 906.25): calculated: C 63.62; H 10.12; N 1.55; found: 63.49; 10.02; 1.81.

Exact chemical name: (2S,3R,4E)-1-[4-0-(β-D-Galactopyranosyl)-β-D-glucopyranosyloxy]-2-[(9Z)-9-octadecenoylamino]-4-octadecen-3-ol

EXAMPLE 2

(2S,3R)-2-(9-cis-12-cis-Octadecadienoylamino)-3-hydroxy-1-(β-D-lactosyloxy)-4-trans-octadecene (11)

1. By the acid chloride method from compounds (5) and (7):

The experimental procedure for the preparation of the compound (11) is analogous to the reaction to give compound (10).

Required: 700 mg (1.129 mmol) of compound (5); 362 μl (1.140 mmol) of linoleoyl chloride (7); 50 ml of tetrahydrofuran, 25 ml of saturated aqueous sodium acetate solution.

The product is purified either (a) via acetylation/deacetylation steps (see Annex, compounds 16 and 17) or (b) by reversed phase medium pressure chromatography (n-butanol/methanol/water 50:32:18). The product is obtained as a colorless foam.

Yield: (a) 640 mg (64%); (b) 710 mg (71%).

2. By the method with 2-ethoxy-1-ethoxycarbonyldihydroquinoline (EEDQ)

230 mg (371 μmol) of compound (5), 115 μl (371 μmol) of linoleic acid and 95 mg (380 μmol) of EEDQ are dissolved in 50 ml of anhydrous ethanol and stirred at 50° C. After 12 hours, no further advance in the reaction is observed. The solution is concentrated, and the crude product is chromatographed on silica gel (chloroform/methanol 85:15).

Yield: 103 mg (58%)

Characterization: Colorless foam of melting point 138°–145° C.

TLC: (Chloroform/methanol 8:2) $R_f$=0.32.
$[\alpha]_D^{20}= -8.7°$ (c=1.1, Pyridine).

Compound (11):
$^1$H NMR (DMSO-d6) 7.51 (d,1H,NH,J=8.3 Hz), 5.57–5.48 (m,1H, HC=CH—CH—OH), 5.39–5.24 (m,5H,HC=CH—CH$_2$, HC=CH—CH$_2$—CH=CH), 5.14 (d,1H,OH,J=4.0 Hz), 5.10 (d,1H,OH,J=3.6 Hz), 4.87 (d,1H,OH, J=5.5 Hz), 4.79 (d,1H,OH,J=4.9), 4.68–4.66 (m,2H,OH), 4.58 (t,1H,OH,J=5.95 Hz), 4.54 (d,1H,OH,J=4.6 Hz), 4.21–3.29 (m,17H), 3.10–3.01 (m,1H), 2.72 (t,2H,HC=CH—CH$_2$—CH=CH), 2.09–1.92 (m,8H,CO—CH$_2$,3 HC=CH—CH$_2$), 1.44–1.23 (m,38H, —CH$_2$—), 0.88–0.83 (2 t,6H,CH$_3$—)

Analysis for C$_{48}$H$_{87}$O$_{13}$N.2.0 H$_2$O (Molecular weight 922.24): Calculated: C 62.51; H 9.95; N 1.52; Found: 62.10; 9.71; 1.67.

Exact chemical name: (2S,3R,4E)-1-[4-0-(β-D-Galactopyranosyl)-β-D-glucopyranosyloxy]-2-[(9Z,12Z)-9,12-octadecadienoylamino]-4-octadecen-3-ol Annex: Product purification via acetylation/deacetylation steps 1. Acetylation (2S,3R)-2-(9-cis-Octadecenoylamino)-3-acetoxy-1-(2,3,6, 2',3',4',6'-hepta-O-acetyl-β-D-lactosyloxy)-4-trans-octadecene (16) and (2S,3R)-2-(9-cis-12-cis-octadecadienoylamino)-3-acetoxy-1-(2,3,6,2',3',4',6'- hepta-o-acetyl-β-D-lactosyloxy) -4-trans-octadecene (17)

400 mg of the impure cerebrosides (10) and (11) are dissolved in 4 ml of anhydrous acetic anhydride and 4 ml of anhydrous pyridine and stirred at room temperature. After 12 hours, acetylation intermediates were no longer detectable by TLC. The solution is concentrated under water pump vacuum and then under high vacuum, and the product is chromatographed on silica gel (petroleum ether/ethyl acetate 1:1). The products are obtained as a colorless solid foam.

TLC: (Petroleum ether/ethyl acetate 1:1) $R_f=0.36$
Melting points: (16): 12° C.; (17): 120° C.
(16): $[\alpha]_D^{20}=-1.8°$ (c=1.3, Chloroform)
(17): $[\alpha]_D^{20}=-0.7°$ (c=1.0, Chloroform)
Compound (16):
$^1$H NMR (CDCl$_3$) 5.86-5.72 (m,1H,HC=CH—CH$_2$), 5.66 (d,1H,NH,J=9.4 Hz), 5.40-5.05 (m,7H,HC=CH—CH—OAc,HC=CH, 4'-H,3-H,2'-H), 4.95 (dd,1H,3'-H,J=3.4 Hz,J=7.7 Hz), 4.85 (dd,1H,2-H,J=7.5 Hz,J=7.7 Hz), 4.55-4.50 (m,3H,1-H,1'-H,4-H), 4.37-4.25 (m, 1H,N—CH), 4.16-4.03 (m,3H,CH$_2$O,5'-H), 3.95-3.75 (m,3H), 3.65-3.45 (m,2H), 2.23-1.93 (m, 32H,8 Acetyl,-COCH$_2$,HC=CH—CH$_2$,CH$_2$—CH=CH—CH$_2$), 1.58 (m,2H,CO—CH$_2$CH$_2$—), 1.19 (s,38H,—CH$_2$—), 0.85 (t,6H,CH$_3$—)

Analysis for C$_{64}$H$_{105}$O$_{21}$N (Molecular weight 1224.53): Calculated: C 62.78; H 8.64; N 1.14; Found: 62.75; 8.68; 1.15;

Compound (17): $^1$H NMR (CDCl$_3$) 5.84-5.72 (m,1H,HC=CH—CH$_2$), 5.65 (d,1H,NH, J=9.15 Hz), 5.40-5.07 (m,9H,HC=CH—CH—OAc,4'—H, 3H,2'—H,HC=CH—CH$_2$—CH=CH), 4.97 (dd,1H,3'—H, J=3.35 Hz,J=8.8 Hz), 4.87 (dd,1H,2—H,J=7.6 Hz, J=7.6 Hz), 4.54-4.41 (m,3H,1—H,1'—H,4—H), 4.32 (m,1H,N—CH), 4.13-4.02 (m,3H,CH$_2$O,5'-H),3.95-3.76 (m,3H), 3.65-3.49 (m,2H), 2.76 (t,1H, HC=CH—CH$_2$—CH=CH,J=6.1 Hz), 2.16-1.96 (m,32H, 8 Acetyl,3 HC=CH—CH$_2$,COCH$_2$), 1.6 (m,2H,CO—CH$_2$—CH$_2$—), 1.25 (m,34H,—CH$_2$—), 0.88 (t,6H,CH$_3$—).

Analysis for C$_{64}$H$_{103}$O$_{21}$N (Molecular weight 1222.51): Calculated: C 62.88; H 8.49; N 1.15; Found: 62.79; 8.44; 1.24.

2. Deacetylation of the compounds (16) and (17)

500 mg of Florisil (magnesium silicate, 200–300 mesh/Fluka AG) are added to 150 mg (122.6 µmol) of the compounds (16) and (17) in 15 ml of anhydrous methanol. The heterogeneous mixture is stirred at 40° C. for 24 hours. After the reaction is complete, 10 ml of chloroform are added, and solids are removed by filtration. Evaporation of the solvent in vacuo results in the product as a colorless foam.

Yield: 108 mg (100%). For characterization of the products, see above.

EXAMPLE 3

2S,3R)-2-(9-cis-12-cis-15-cis-Octadecatrienoylamino)-3-hydroxy-1-(β-D-lactosyloxy)-4-trans-octadecene (12)

By the acid chloride method, from compounds (5) and (8):

The experimental procedure for the preparation of the compound (12) is analogous to the reaction to give compound (10).

Required: 600 mg (967 µmol) of compound (5): 307 µl (966 µmol) of linoleoyl chloride (8) 50 ml of tetrahydrofuran/25 ml of saturated aqueous sodium acetate solution.

The product is purified by reverse phase medium pressure chromatography (n-butanol/methanol/water 50:32:18).

Yield: 635 mg (74%) of colorless foam of melting point 145°-151° C.

TLC: (Chloroform/methanol 8:2) $R_f=0.32$
$[\alpha]_D^{20}=-4.6°$ (c=1.15, Pyridine)
Compound (12):
12 $^1$H NMR (DMSO-d6) 7.56 (d,1H,NH,J=8.9 Hz), 5.60-5.48 (m,1H, HC=CH—CH—OH), 5.38-5.25 (m,7H,HC=CH—CH$_2$,3 HC=CH), 5.16 (d,1H,OH,J=3,7 Hz), 5.13 (d, 1H,OH,J=3,6 Hz), 4.89 (d,1H,OH,J=5.5 Hz), 4.82 (d,1H,OH,J=3.7 Hz), 4.67 (m,2H,OH), 4.59 (t,1H,OH,J=5.95 Hz), 4.54 (d,1H,OH, J=4.21-3.29 (m,17H), 3.07-3.06 (m,1H), 2.79-2.74 (t,4H,2 HC=CH—CH$_2$—CH=CH) 2.10-1.92 (m,8H,COCH$_2$,3 HC=CH—CH$_2$), 1.48-1.43 (m,2H,CO—CH$_2$—CH$_2$—), 1.36-1.23 (m, 30H,—CH$_2$—), 0.93 (t,3H,HC=CH—CH$_2$—CH$_3$,J=7.7 Hz), 0.85 (t,3H,CH$_3$—,J=6.6 Hz)

UV spertrum:

To estimate the proportion of conjugated systems, the extinctions are compared with standard figures for absorption of conjugated unsaturated carboxylic acids [J. Amer.Chem.Soc. 66 (1944), 287–289]. The following extinction coefficients are found in compounds of these types [Proc.Natl.Acad.Sci. U.S. 69 (1972), 3561–3566].

| | | |
|---|---|---|
| $\lambda_1$ = 232 nm | ($\epsilon$ = 33600) | Diene |
| $\lambda_2$ = 270 nm | ($\epsilon$ = 46700) | Triene |
| $\lambda_3$ = 320 nm | ($\epsilon$ = 57700) | Tetraene |

The extinction coefficients measured in the UV spectrum of compound (12) were as follows.

| | |
|---|---|
| $\lambda_1$ = 232 nm | $\epsilon$ = 323 |
| $\lambda_2$ = 270 nm | $\epsilon$ = 70 |
| $\lambda_3$ = 320 nm | $\epsilon$ = 29 |

The maximum percentages resulting from this are 0.95% for conjugated dienes, 0.15% for conjugated trienes and 0.05% for conjugated tetraenes, as a proportion of the total product.

Analysis for C$_{48}$H$_{85}$O$_{13}$N.1.0 H$_2$O (Molecular weight 902.22): Calculated: C 63.90; H 9.72; N 1.55; Found: 63.43; H 9.92; N 1.62.

Exact chemical name: (2S,3R,4E)-1-[4-0-(β-D-Galactopyranosyl)-β-D-glucopyranosyloxy -oxy]-2-[(9Z,12Z,15Z)-9,12,15-octadecatrienoylamino]-4-octadecen-3-ol

EXAMPLE 4

(2S,3R)-2-(5-cis-8-cis-11-cis-14-cis-Eicosatetraenoylamino)
-3-hydroxy-1-(β-D-lactosyloxy)-4-trans-octadecene (13)

By the acid chloride method, from compounds (5) and (9):

The reaction of the acid chloride with compound (5) is analogous to the preparation of compound (10).

---

The reaction of the acid chloride with compound (5) is analogous to the preparation of compound (10).

-continued

Required: 53.1 mg of arachidonol chloride (9) (164 μmol)
102 mg of compound (5) (164 μmol)
10 ml of tetrahydrofuran/5 ml of saturated
aqueous sodium acetate solution.

The compound (13) is purified by reversed phase medium pressure chromatography (n-butanol/methanol/water 50:32:18).

Yield: 110 mg (74%) of colorless foam.

TLC: (Chloroform/methanol 72:28) $R_f=0.49$

Melting point: from 115° to 135° C. with decomposition

Compound (13):

$^1$H NMR (DMSO-d6) 7.52 (d,1H,NH,J=9.0 Hz), 5.55-5.49 (m,1H, HC=CH—CH$_2$), 5.39-5.32 (m,9H,HC=CH—CH—OH, 4 HC=CH), 5.13 (d,1H,OH,J=3.9 Hz), 5.10 (d,1H,OH,J=4.6 Hz), 4.87 (d,1H,OH,J=5.3 Hz), 4.78 (d,1H,OH,J=4.9 Hz), 4.67-4.65 (d,t,2H,OH), 4.57 (t,1H,OH,J=6.0 Hz), 4.19 (d,1H,1-H,J=7.1 Hz), 4.15 (d,1H,1 -H,J=7.8 Hz), 4.00-3.96 (m,1H), 3.92-3.87 (m,1H), 3.82-3.72 (m,2H), 3.63-3.61 (m,2H), 3.58-3.28 (m,9H), 3.06-3.02 (m,1H), 2.81-2.76 m,6H,3 HC=CH—CH$_2$—CH=CH), 2.09-1.97 (m,6H, 3 HC=CH—CH$_2$),1.93-1.91 (m,2H,COCH$_2$), 1.54-1.49 (m,2H,CO—CH$_2$—CH$_2$13 ), 1.35-1.23 (m, 28H,—CH$_2$—), 0.87-0.83 (2 t,6H,CH$_3$—).

UV spectrum: The UV spectrum was evaluated in analogy to that of compound (12). The maximum proportion of conjugated dienes is 2.1%, that of conjugated trienes is 0.6% and that of conjugated te... is 0.2%.

Analysis for $C_{50}H_{87}O_{13}N \cdot 2.0\ H_2O$ (M... weight 946.27): Calculated: C 63.46; H 9.69; N 1.48; Found: 63.06; 9.80; 1.62.

Exact chemical name: (2S,3R,4E)-1-14-0-(β-D-Galactopyranosyl)-β-D-glucopyranosyl -oxy]-2-[(5Z,8Z,11Z,14Z)-5,8,11,14-eicosatetraenoylamino]-4-octadecen-3-ol

EXAMPLE 5

(2S,3R)-2-(5-cis-8-cis-11-cis-14-cis-Eicosatetraenoylamino)
-3-hydroxy-1-(β-D-lactosyloxy)-4-trans-octadecene (13)

150 mg (242 μmol) of compound (5) and 1.17 ml (3.63 mmol) of arachidonoyl chloride—compound (9)—are dissolved in 15 ml of anhydrous pyridine. After addition of a spatula tip of 4-dimethylaminopyridine, the reaction mixture is stirred at 75° C. for 2 days (TLC check). The mixture is evaporated to dryness, and the product is purified by medium pressure chromatography (petroleum ether/ethyl acetate 92:8) and treated with sodium methanolate. The resulting compound (13) has the same properties as indicated in Example 4.

EXAMPLE 6: INJECTABLE SOLUTION 5 of g Pluronic(®) F 68 and 500.mg of the compound Lac(Pal)-D-Sph - (2S,3R,4E)-1-[4-0-(8-D-galactopyranosyl) -β-D-glucopyranosyloxy]-2-hexadecanoylamino-4-octadecen-3-ol—are dissolved with stirring in 100 ml of physiological saline (0.9% NaCl), and the solution is sterilized by filtration through a Millipore 22 filter and dispensed in 1 ml portions into ampoules. One ampoule contains 5 mg of the above-mentioned active ingredient.

EXAMPLE 7: GEL (a) 100 mg of the compound Lac(Ol)-D-Sph (see Example 1) are dissolved in 50 ml of demineralized water, and to the solution are added firstly 3 g of diisopropylamine and then, slowly with stirring, 3 g of Carbopol® 940 (polyacry acid of average molecular weight 4,000,000; manufactured by Goodrich Chemical Co., Cleveland OH/USA), and the mixture is left to stand overnight and then made up to a final volume of 100 ml by slow addition of demineralized water while stirring continuously. 1 g of gel contains 1.0 mg of active ingredient.

(b) 2.0 g of diisopropanolamine are dissolved in 10 g of demineralized water, forming solution A. In addition, 50 g of 95% ethanol and 5.0 g of diisopropyl adipate, as lubricant, are mixed together and, while stirring, 200 mg of the compound Lac(Pal)-L-Sph are dissolved therein, and solution A is added slowly until a pH of 6.8 is reached (solution B).

2 g of Carbopol® 941 (polyacrylic acid of molecular weight 1,250,000) are mixed with 20 parts of demineralized water and the mixture is left to swell for some time and then stirred until a homogeneous mass has formed, and solution A is added, with stirring, until the pH has been adjusted to 6.8; a gel C is produced.

Solution B is now slowly mixed, with continuous stirring, into the gel C in order to form a homogeneous gel and, finally, demineralized water is added to a final weight of 100 g. A gel containing 2.0 mg of active ingredient per 1 g is obtained.

EXAMPLE 8: OINTMENT 500 mg of the compound Lac(Linol)-D-Sph (see Example 2) are suspended in 35 g of high viscosity paraffin, and 35 g of cetylstearyl alcohol and 30 g of white petrolatum are added to the suspension and the mixture is slowly heated in a waterbath to the melting point, the molten mass is stirred at a slow speed (about 60 rpm) at the same temperature for 20 minutes, the heating is switched off, and stirring of the mass is continued until cold. 1 g of ointment contains 5 mg of active ingredient.

EXAMPLE 9: CREAM

Firstly, a homogeneous mixture of 12 g of 1-propyloxypropane-2,3-diol, 6 g of 1-n-hexyloxypropane -2,3-diol, 6 g of 1-n-nonyloxypropane-2,3-diol, 24 g of water and 1.0 g of phenoxyethanol is prepared by stirring vigorously. 1.0 g of the compound Lac(Linolen)-D-Sph (see Example 3) is added to the mixture and dissolved by stirring. In addition, 30 g of white petrolatum, 15 g of cetyl alcohol and 5 g of sorbitan monopalmitate are mixed and melted in a waterbath by slowly heating to a temperature of about 70° C. The active ingredient solution, which has likewise been heated to about 70° C., is now dispersed in the molten mass by stirring at high speed, and the mixture is allowed to cool while stirring continues. A water-in-oil emulsion (cream) which contains 10 mg of active ingredient in 1 g is obtained.

EXAMPLE 10: INJECTABLE SOLUTION 2 g of Pluronic® F 68 are dissolved in 100 ml of physiological saline, and 2 g of the compound Lac-(Arach)-D-Sph (see Example 4) are added to the solution and dissolved by stirring, and the solution is sterilized by filtration through a Millipore 22 filter and dispensed in 1 ml portions into ampoules. One ampoule contains 20 mg of active ingredient.

Preparation of the Starting Materials

D-threo-Sphingosine can be prepared by the process of P. Herold [Helv. Chim.Acta 71 (1988), 354–362].
Synthesis of L-threo-sphingosine
(2S,3S,4E)-2-Amino-1,3-dihydroxy-4-octadecene 2,4-O-Benzylidene-D-threose—Compound (1) and 2,4-O-Benzylidene-D-erythrose—Compound (14)

Preparation of a phosphate buffer of pH 7.6: 10.4 g of $NaH_2PO_4.2\ H_2O$ are dissolved in 700 ml of water and the pH is adjusted to 7.6 with 1N sodium hydroxide solution. The solution is now made up to 1 liter with water.

5 g of 4,6-O-benzylidene-D-galactose or 4,6-O-benzylidene-D-glucose are dissolved in 300 ml of phosphate buffer of pH 7.6. Now 9.25 g (43.2 mmol) of sodium periodate are added in portions. The pH is maintained between 7.5 and 7.7 by continuous dropwise addition of 2N sodium hydroxide solution (stirring vigorously). After the sodium periodate has been added, the foaming solution is stirred for another 2 hours. The clear solution is now evaporated to dryness under waterpump vacuum. The residue is extracted with tetrahydrofuran (about 3 x 150 ml), concentrated and dried under high vacuum.

Yield: 3.3 g (85%) of compound (2); 3.4 g (87%) of compound (14).

TLC: (toluene/ethanol 3:1) Rf: 0.66
Melting point: 158 to 161° C. for compound (1)
Melting point: 140 to 145° C. for compound (4)

1,3-O-Benzylidene-(2R,3S)-1,2,3-trihydroxy-4-transoctadecene Compound (15)

70 g of tetradecylphosphonium bromide are added under a nitrogen atmosphere to 1 liter of anhydrous toluene. The mixture is cooled to −30° C. and then freshly prepared phenyllithium in diethyl ether (from 5.4 g of lithium and 62 g of bromobenzene) is rapidly added dropwise, stirring vigorously. The solution becomes orange in color. Then 16 g (76.8 mmol) of compound (14) in tetrahydrofuran are slowly added dropwise. After the dropwise addition, the mixture is stirred at −30° C. for 5 minutes and then at room temperature for 20 minutes. The brown solution is first diluted with methanol and then water is added. The organic phase is separated off and concentrated under waterpump vacuum, and the residue is applied to a silica gel column (petroleum ether/ethyl acetate 4:1) for purification.

Yield: 18 g (60% of theory).
TLC: (Petroleum ether/ethyl acetate 4:1) $R_f=0.18$
Melting point: 38 to 39° C.
Analysis for $C_{25}H_{40}O_3$ (Molecular weight 388.6):
Calculated: C 77.27; H 10.38;

| Calculated: | C 77.27 | H 10.38 |
|---|---|---|
| Found: | 77.0 | 10.47 |
| | 77.02 | 10.17 |

$^1$H NMF Spectrum (in $CDCl_3$): 7.51–7.28 (m, 5H, aromat.); 6.0–5.88 (m, 1H,—CH=CH—OH); 5.36 (s, 1H, Ph—CH—); 5.62–5.48 (dd, 1H, CH=CH OH, $J_{trans}$=15.5 Hz, $J_{vic}$=6.8); 4.4–4.3 (dd, 1H, CH=CH—CHO); 3.97–3.98 (m, 1H,—CH—OH); 3.69–3.6 (m, 2H,—CH$_2$—O); 2.14–2.06 (m, 2H, CH=CH—CH$_2$); 1.75–1.68 (d, 1H,—OH, $J_{vic}$=3 Hz); 1.5–1.23 (m, 22H, aliphat.); 0.93–0.85 (t, 3H,—CH$_3$).

2-Azido-1,3-0-benzylidene-(2S,3S)-1,3-dihydroxy-4-transoctadecene—Compound (16)

200 ml of anhydrous methylene chloride and 3.3 ml of anhydrous pyridine are cooled under a nitrogen atmosphere to −15° C. 12 g (31 mmol) of compound (15) are added to this solution. Then 5.56 ml (35 mmol) of trifluoromethanesulfonyl chloride are added dropwise. After stirring vigorously for 5 minutes (the solution becomes dark red), 200 ml of amine-free dimethylformamide and 8 g of sodium azide (about 10 molar excess) are added. The reaction mixture is stirred vigorously for 2 hours and then poured into about 200 ml of water, the mixture is extracted with petroleum ether (3 x 100 ml), and the organic phase is dried over magnesium sulfate and evaporated under waterpump vacuum. The residue is applied to a silica gel column (petroleum ether/ethyl acetate 9:1) for purification.

TLC: (Petroleum ether/ethyl acetate 9:1) $R_f$=0.58
$^1$H NMR-spectrum: (in $CDCl_3$): 7.54–7.38 (m, 5H, aromat.); 4.86 (s, 1H, Ph—CH—); 5.96–5.82 (m, 1H, CH=CH—OH); 5.57–5.44 (dd, 1H, CH=CH—OH, $J_{trans}$=15.8 Hz, $J_{vic}$=7 Hz); 4.75–4.65 (dd, 1H, CH=CH—CHO, $J_1$=$J_2$=6 Hz), 4.39–4.38 (m, 1H, CH—N$_3$); 4.48–3.38 (dd, 1H, O—CH$_2$—C); 3.4–3.25 (dd, 1H, O—CH$_2$—C); 2.18–4.05 (m, 2H, CH=CH—CH$_2$); 1.45–1.15 (m, 22H, aliphat.); 0.93–0.85 (t, 3H, CH$_2$).

Because of its instability, compound (16) was used immediately for subsequent reactions.

(2S,3S)-2-Azido-1,3-dihydroxy-4-transoctadecene—Compound (17)

The synthesis was carried out as described in EP 212,400, page 22, for (2S,3R)-2-azido-1-hydroxy-4-transoctadecene, starting from compound (16).

Yield: 50 mg (68% of theory)
TLC: (methylene chloride/methanol 95:5) $R_f$=0.36
Analysis for $C_{18}H_{35}C_2N_3$ (Molecular weight 325.5):
Calculated: C 66.42; H 10.84; Found: 66.90; 10.99.

$^1$H NMR-Spectrum (in $CDCl_3$): 5.86–5.75 (m, 1H,—CH=CH—CHOH); 5.53–5.44 (dd, 1H,—CH=CH—CHOH, $1_{trans}$=14.5 Hz, $J_{vic}$=6.5 Hz); 4.18–4.11 (dd, 1H;—CH=CH—CHOH); 3.8–3.73 (m, 1H,—CH—N$_3$); 3.42–3.36 (m, 2H,—CH$_2$—OH); 2.29–2.27 (d, 1H,—OH); 2.17–2.05 (m, 2H, CH=CH—CH$_2$); 1.91–1.89 (d, 1H,—OH); 1.37–1.2 (m, 22H, aliphat.); 0.98–0.85 (t, 3H,—CH$_3$).

(2S,3S)-2-Amino-1,3-dihydroxy-4-transoctadecene—Compound (18)

50 mg (0.16 mmol) of compound (17) are dissolved in 10 ml of pyridine containing 1 ml of water and, while stirring, hydrogen sulfide is introduced (H2S from NaHS). After 2 hours, the solvent mixture is removed in vacuo, and the residue is recrystallized twice from a little acetonitrile.

Yield: 38 mg (95% of theory)
TLC: (chloroform/methanol/2N NH$_3$ 40:10:1)
$R_f$=0.44
Detection with ninhydrin
$^1$H NMR-Spectrum (in $CDCl_3$): 5.88–5.72 (m, 1H,—CH=CH—CHOH); 5.55–5.42 (dd, 1H,—CH=CH—CHOH, $J_{trans}$=15 Hz, $J_{vic}$=7 Hz); 4.2–4.2 (dd, 1H, CH=CH—CHOH, $J_1$=$J_2$=5.5 Hz); 3.8–3.7 (m, 1H,—CH—NH$_2$); 3.45–3.35 (m, 2H,—CH$_2$—OH); 1.85–1.6 (m, 6H, CH=CH—CH$_2$,—NH$_2$, 2 mol—OH); 1.42–1.11 (m, 22H, ali—phat.); 0.95–0.85 (t, 3H,—CH$_3$).

Reaction with a phosphonate

(a) Diethyl tetradecane-1-phosphonate 100 g (590 mmol) of triethyl phosphite and 164 g (590 mmol) of 1-bromotetradecane are heated on a column connected to a descending condenser. Bromoethane distills out at a bath temperature of 170° C.; the mixture is then distilled under high vacuum, resulting in the product of boiling point 145° C./0.03 mmHg which is pure by $^1$H NMR.

(b) (2S,3R,4E)-1,3-0-Benzylidene-1,2,3-trihydroxy-4-octadecene 16.6 g (50 mmol) of diethyl tetradecane-1-phosphonate are dissolved in 10 ml of anhydrous tetrahydrofuran and cooled to $-40°$ C. with a protective gas atmosphere. 1.6 g (25 mmol, in tetrahydrofuran) of n-butyllithium are slowly added dropwise to the resulting heterogeneous mixture and, at the same time, the temperature is lowered to $-50°$ C. Then 10 g (46.6 mmol) of 2,4-0-benzylidene -D-threose, dissolved in 10 ml of tetrahydrofuran, are slowly added dropwise. After 1 hour (TLC check) the reaction solution is warmed to room temperature and poured into 20 ml of water. The phases are separated, and the organic phase is dried over magnesium sulfate and concentrated in vacuo. The resulting oil is dissolved in 5 ml of ethyl acetate, and acidic ion exchanger (Amberlite IR 120) which has been washed acid-free several times with methanol is added. The elimination reaction is complete after stirring at room temperature for 5 hours. The ion exchanger is removed by filtration, and the filtrate is concentrated and chromatographed (petroleum ether/ethyl acetate 9:1).

TLC: (petroleum ether/ethyl acetate 9:1) $R_f = 0.21$

The resulting product is identical by $^1$H NMR spectroscopy to the compound obtained by the method of R. R. Schmidt et al., Tetrahedron Letters 27 (1986), 481.

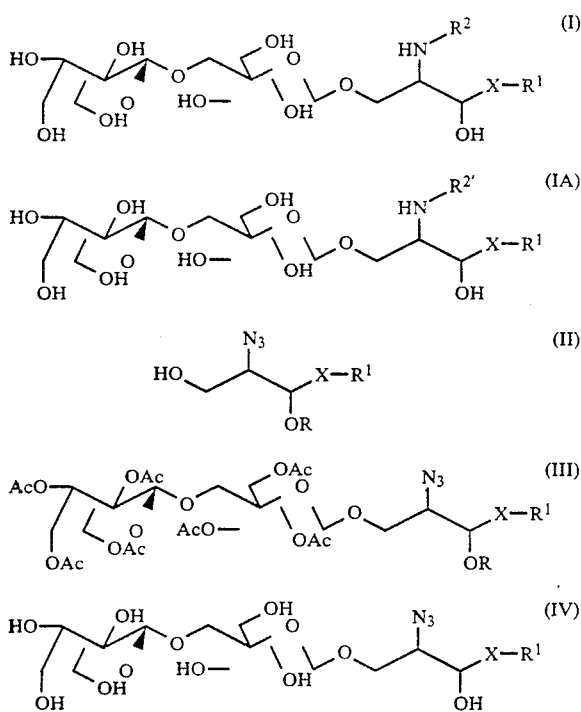

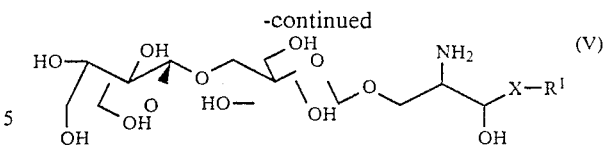

We claim:

1. A pharmaceutical composition useful as a cytoprotective agent, which comprises:
   an effective amount of a lactosyl compound of the formula I

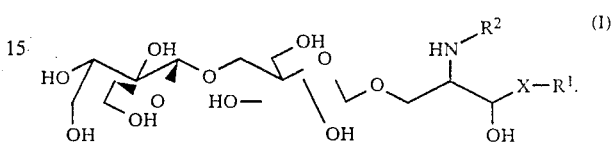

in which $R^1$ denotes an aliphatic radical which has 9 to 19 carbon atoms in a straight chain and which can have one or more double bonds, one or more branching methyl groups, or both one or more double bonds and one or more branching methyl groups, $R^2$ denotes an acyl radical of a singly or multiply unsaturated fatty acid having 14 to 24 carbon atoms, and X denotes a group of the formula —CH$_2$—CH$_2$—or —CH=CH—, and
   a member selected from the group consisting of pharmaceutically acceptable excipients and auxiliaries and mixtures thereof.

2. A composition as claimed in claim 1, in which the aliphatic radical $R^1$ in the lactosyl compound has 13 to 15 carbon atoms in the straight chain.

3. A composition as claimed in claim 1, in which the acyl radical $R^2$ in the lactosyl compound has an even number of carbon atoms.

4. A composition as claimed in claim 3, in which $R^2$ in the lactosyl compound is an acyl radical having 16, 18 or 20 carbon atoms in the straight chain.

5. A lactosyl compound of the formula IA

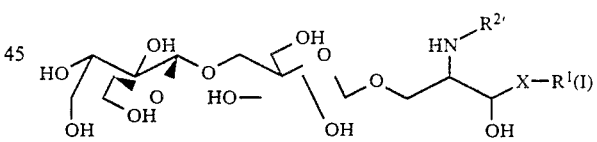

in which $R^1$ denotes an aliphatic radical which has 9 to 19 carbon atoms in a straight chain and which can have one or more double bonds, one or more branching methyl groups, or both one or more double bonds and one or more branching methyl groups, $R^{2'}$ denotes an acyl radical of a singly or multiply unsaturated fatty acid having 14 to 24 carbon atoms, and X denotes a group of the formula —CH$_2$—CH$_2$—or —CH=CH—.

6. A lactosyl compound as claimed in claim 5, in which the aliphatic radical $R^1$ has 13 to 15 carbon atoms in the straight chain.

7. A lactosyl compound as claimed in claim 5, in which the acyl radical $R^{2'}$ has an even number of carbon atoms.

8. A lactosyl compound as claimed in claim 7, in which $R^{2'}$ is an acyl radical having 16, 18 or 20 carbon atoms in the straight chain.

9. A method of treating acute or chronic inflammation in a subject, which comprises administering to the subject a therapeutically effective amount of a lactosyl compound of the formula I

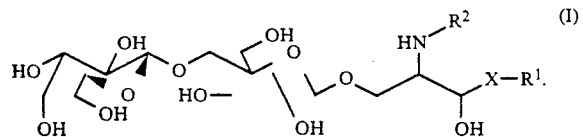

in which $R^1$ denotes an aliphatic radical which has 9 to 19 carbon atoms in a straight chain and which can have one or more double bonds, one or more branching methyl groups, or both one or more double bonds and one or more branching methyl groups, $R^2$ denotes an acyl radical of a saturated or singly or multiply unsaturated fatty acid having 14 to 24 carbon atoms, and X denotes a group of the formula $-CH_2-CH_2-$ or $-CH=CH-$.

10. A method of treating organ ischemia caused by narrowing of vessels in a subject, which comprises administering to the subject a therapeutically effective amount of a lactosyl compound of the formula I

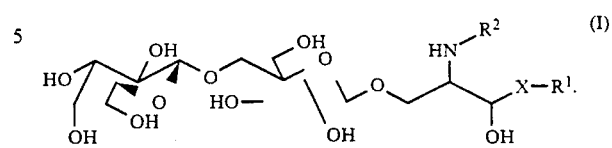

in which $R^1$ denotes an aliphatic radical which has 9 to 19 carbon atoms in a straight chain and which can have one or more double bonds, one or more branching methyl groups, or both one or more double bonds and one or more branching methyl groups, $R^2$ denotes an acyl radical of a saturated or singly or multiply unsaturated fatty acid having 14 to 24 carbon atoms, and X denotes a group of the formula $-CH_2-CH_2-$ or $-CH=CH-$.

* * * * *